(12) United States Patent
Aoki et al.

(10) Patent No.: US 9,818,030 B2
(45) Date of Patent: Nov. 14, 2017

(54) OPHTHALMIC DEVICE AND METHOD FOR CONTROLLING THE SAME

(71) Applicant: Tomey Corporation, Nagoya-shi (JP)

(72) Inventors: Nobuyori Aoki, Nagoya (JP); Tsutomu Ohmori, Nagoya (JP); Naoko Hara, Nagoya (JP); Chihiro Kato, Nagoya (JP)

(73) Assignee: Tomey Corporation, Nagoya-shi (JP)

( * ) Notice: Subject to any disclaimer, the term of this patent is extended or adjusted under 35 U.S.C. 154(b) by 0 days.

(21) Appl. No.: 15/010,149

(22) Filed: Jan. 29, 2016

(65) Prior Publication Data
US 2016/0224831 A1    Aug. 4, 2016

(30) Foreign Application Priority Data
Jan. 30, 2015  (JP) ................. 2015-016369

(51) Int. Cl.
| | |
|---|---|
| *A61B 3/14* | (2006.01) |
| *G06K 9/00* | (2006.01) |
| *A61B 3/10* | (2006.01) |
| *A61B 3/113* | (2006.01) |
| *A61B 3/12* | (2006.01) |
| *G06T 7/20* | (2017.01) |

(52) U.S. Cl.
CPC .......... *G06K 9/00604* (2013.01); *A61B 3/102* (2013.01); *A61B 3/113* (2013.01); *A61B 3/12* (2013.01); *G06T 7/20* (2013.01); *G06T 2207/10004* (2013.01); *G06T 2207/30041* (2013.01)

(58) Field of Classification Search
CPC ........... A61B 3/102; A61B 3/113; A61B 3/10; A61B 3/12; G06K 9/00604; G06T 7/20; G06T 2207/3004; G06T 2207/10004
USPC ................. 351/209, 208, 205, 200
See application file for complete search history.

(56) References Cited

U.S. PATENT DOCUMENTS

| | | | | |
|---|---|---|---|---|
| 7,747,068 | B1 * | 6/2010 | Smyth ..................... | G03B 17/00 382/154 |
| 2008/0212028 | A1 * | 9/2008 | Ichikawa ................. | A61B 3/14 351/208 |
| 2013/0195337 | A1 | 8/2013 | Sakagawa | |

FOREIGN PATENT DOCUMENTS

JP           200829467         2/2008

\* cited by examiner

*Primary Examiner* — Tuyen Tra
(74) *Attorney, Agent, or Firm* — Jeffrey D. Myers; Peacock Myers, P.C.

(57) ABSTRACT

An ophthalmic device capable of obtaining B-scan graphical images at high speed while eliminating positional displacement due to movement of a subject eye. The device includes: anterior eye image obtaining means configured to obtain an image of an anterior eye of a subject eye; eye fundus image obtaining means configured to obtain an image of an eye fundus of the subject eye; and control means configured to detect a moving distance of the subject eye in the anterior eye image using means configured to calculate correlation between a moving distance of the subject eye in the anterior eye image and a moving distance in the eye fundus image, and to control a position for imaging of the eye fundus image based on the detected moving distance of the subject eye and the calculated correlation.

12 Claims, 12 Drawing Sheets

Fig. 7A
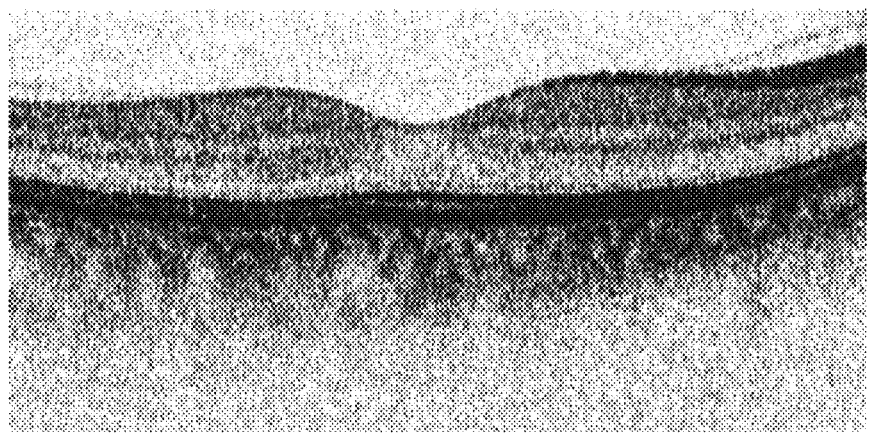
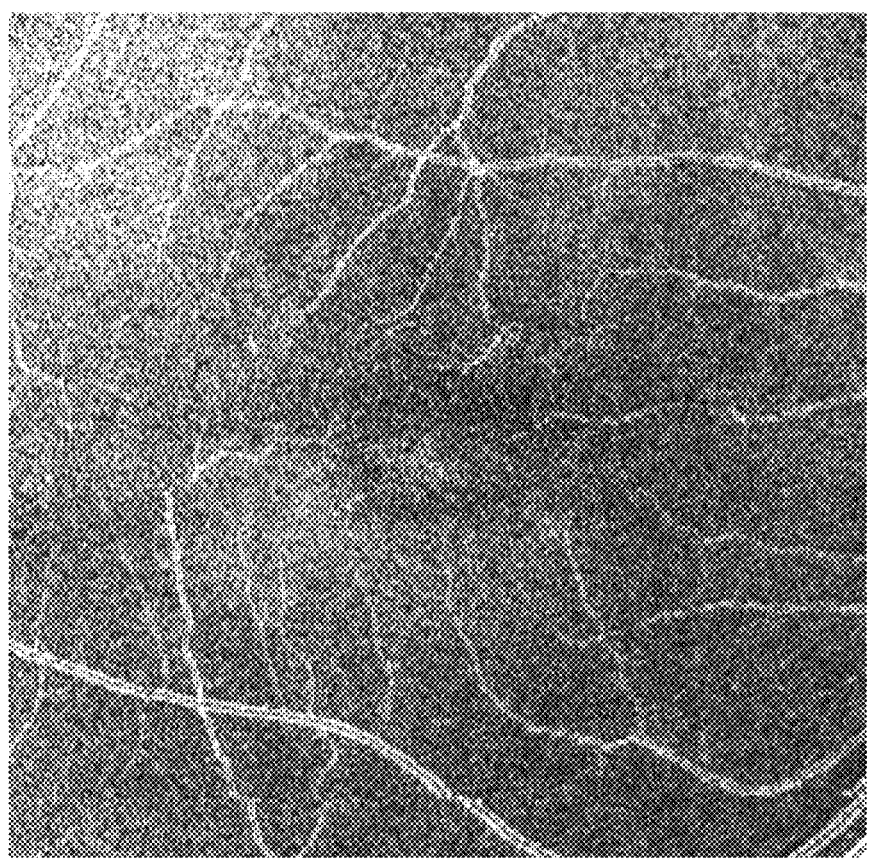
Fig. 7B

ANTERIOR EYE IMAGE

OPHTHALMIC DEVICE AND METHOD FOR CONTROLLING THE SAME

CROSS-REFERENCE TO RELATED APPLICATIONS

This application claims priority to and the benefit of the filing of Japanese Patent Application No. 2015-016369, filed on Jan. 30, 2015, and the specification and claims thereof are incorporated herein by reference.

TECHNICAL FIELD

The present invention relates to an ophthalmic device and a method for controlling the ophthalmic device.

BACKGROUND ART

Optical Coherence Tomography (hereinafter also referred to as "OCT") is a method for measuring a tomographic image of a living body using optical coherence, and is widely used for obtaining two-dimensional/three-dimensional tomographic images of corneas and retinas especially in the field of ophthalmology. Commonly, in OCT, two-dimensional images are called B-scan images, and three-dimensional images are called C-scan images. Therefore, a two-dimensional image is called a B-scan (graphical) image, and a three-dimensional image is called a C-scan (graphical) image, hereinafter.

Typically, a device for taking tomographic images of a subject eye is provided with, in addition to an OCT optical system, an optical system for obtaining other front images of an eye (e.g., front images of eye fundus and front images of cornea surface). For example, fundus cameras or Scanning Laser Ophthalmoscope (SLO) are employed for imaging of front images of eye fundus. The front images taken by a fundus camera or an SLO is used in observation of a configuration of an entire cornea or retina, in positioning when obtaining a tomographic view in OCT, and in correction of positional displacement of an obtained OCT image.

If a subject eye moves during OCT imaging, motion artifact is produced in an OCT tomographic image that has been obtained, and it is not possible to obtain an accurate OCT tomographic image. Therefore, conventionally, front images taken by a fundus camera or an SLO are used to calculate a moving distance of the subject eye, and thus tracking in the OCT imaging or correction of positional displacement in an obtained OCT image is performed using the calculated moving distance.

Japanese Publication No. 2008-029467 discloses one example of the above. Specifically, even if the subject eye moves during measurement, it is possible to observe a certain tomographic view (B-scan image) without any influence of the movement by switching irradiation every time a single OCT B-scan graphical image is obtained to obtain an SLO eye fundus image, and correcting positional displacement of an OCT B-scan graphical image using the obtained SLO eye fundus image.

SUMMARY OF THE INVENTION

Technical Problems

The method disclosed in Japanese Publication No. 2008-29467 and the conventional method performs tracking in the OCT imaging only using an SLO image (eye fundus image). However, timing of tracking is restricted by timing at which an SLO image is obtained. Therefore, there is a problem that when the OCT imaging is performed at timing faster than the SLO imaging, it is not possible to perform the OCT tracking accurately, and motion artifact may often be produced in the obtained OCT image.

Further, according to the method disclosed in Japanese Patent Publication No. 2008-29467, there is another problem that as an SLO eye fundus image is obtained every time a single OCT B-scan graphical image is obtained, it takes an extended period of time to take three-dimensional tomographic views in the OCT imaging in which several hundreds of B-scan graphical images are obtained.

Moreover, in the case of Doppler OCT in which blood flow in the eye fundus is measured using OCT, it is necessary to obtain OCT B-scan graphical images at pre-determined time intervals according to speed of the blood flow to be measured. There is another problem that according to the conventional method disclosed in Japanese Patent Publication No. 2008-29467, it is not possible to measure the blood flow accurately, as control of tracking relating to the OCT imaging is restricted by timing for imaging of eye fundus by the SLO or a fundus camera.

The present invention is made in view of the above problems, and aims to provide an ophthalmic device capable of obtaining B-scan graphical images at high speed while eliminating positional displacement due to movement of the subject eye.

Solution to Problems

In order to achieve the above object, an ophthalmic device according to one embodiment of the present invention includes: anterior eye image obtaining means configured to obtain an image of an anterior eye of a subject eye; eye fundus image obtaining means configured to obtain an image of an eye fundus of the subject eye; and correlation calculating means configured to calculate correlation between a moving distance of the subject eye in the anterior eye image and a moving distance in the eye fundus image.

Further, in order to achieve the above object, an ophthalmic device according to another embodiment of the present invention is provided, in which the eye fundus image obtaining means includes at least two eye fundus image obtaining means each configured to obtain an image of the eye fundus of the subject eye, and the correlation calculating means calculates correlation between the moving distance of the subject eye obtained by the anterior eye image obtaining means and the moving distance in the eye fundus image taken by one of the at least two eye fundus image obtaining means.

Moreover, in order to achieve the above object, an ophthalmic device according to another embodiment of the present invention is provided including: control means configured to control a position for imaging of the eye fundus image by the at least one eye fundus image obtaining means based on the moving distance of the eye fundus image calculated from the moving distance of the subject eye in the anterior eye image using the correlation calculated by the correlation calculating means and/or the moving distance of the eye fundus image calculated from the eye fundus image obtained by the eye fundus image obtaining means.

Furthermore, in order to achieve the above object, an ophthalmic device according to another embodiment of the present invention is provided including: positional displacement correction means configured to perform correction of positional displacement of the eye fundus image after imaging by the at least one eye fundus image obtaining means based on the moving distance of the eye fundus image calculated from the moving distance of the subject eye in the anterior eye image using the correlation calculated by the correlation calculating means and/or the moving distance of the eye fundus image calculated from the eye fundus image obtained by the eye fundus image obtaining means.

Additionally, in order to achieve the above object, an ophthalmic device according to another embodiment of the present invention is provided, in which the correlation calculating means includes calculating means configured to obtain a plurality of anterior eye images and a plurality of eye fundus images (by the at least one eye fundus image obtaining means) for a predetermined time period, and to calculate correlation between a moving distance of the subject eye and a moving distance in the eye fundus image (due to the movement of the subject eye) from the plurality of obtained anterior eye images and the plurality of obtained eye fundus images.

Further, in order to achieve the above object, an ophthalmic device according to another embodiment of the present invention is provided, in which, when obtaining and recording the plurality of anterior eye images and the plurality of eye fundus images (by the at least one eye fundus image obtaining means), the correlation calculating means also records time of the obtaining.

Moreover, in order to achieve the above object, an ophthalmic device according to another embodiment of the present invention is provided, in which the correlation calculating means obtains the anterior eye images and the eye fundus images (by the at least one eye fundus image obtaining means) at the same time at at least two different times.

For example, the correlation between a moving distance of the anterior eye (e.g., a front side of the cornea) and a moving distance of the eye fundus (e.g., a retina position) is calculated based on information on an average eye or a measured subject eye (such as a value of an axial length), and recorded in the device. Then, an anterior eye image is taken using a high frame-rate imaging device to detect the movement of the subject eye (moving distance), and a moving distance of the eye fundus position is calculated based on the detected moving distance and the recorded correlation, and a position for taking the eye fundus image is controlled based on the moving distance of the eye fundus position calculated from this correlation in addition to the moving distance of the conventional eye fundus image. Therefore, it is possible to perform imaging position control at high speed, allowing responding to very quick movement of the subject eye.

In a case in which the two eye fundus image obtaining means are an SLO and an OCT, for example, using the anterior eye image and the SLO eye fundus image, correlation between the movement of the anterior eye (moving distance) and the movement of the eye fundus (moving distance) is previously calculated and recorded. Then, when performing OCT measurement, the OCT scanning is controlled based on, in addition to the moving distance of the conventional eye fundus image, the moving distance of the eye fundus calculated using the method of detecting the movement of the anterior eye image and using the correlation. Therefore, it is possible to reduce an influence of the movement of the subject eye and to obtain B-scan graphical images.

For example, before the OCT measurement, by obtaining a plurality of anterior eye images and a plurality of eye fundus images of the subject eye for a predetermined time period, and by obtaining correlation between an amount of the movement of the anterior eye (moving distance) and an amount of the movement of the eye fundus (moving distance) from the plurality of obtained anterior eye images and the plurality of obtained eye fundus images, correlation between the anterior eye and the eye fundus of the subject eye to be measured is obtained immediately before the measurement. With this, the (OCT) imaging position may be controlled more accurately.

The timing for obtaining the anterior eye image and the timing for obtaining the eye fundus image are not necessarily identical. In order to calculate the correlation between the moving distances, it is necessary to extract images of identical time among a plurality of images taken at identical timing (meaning that time is identical). Therefore, it is possible to facilitate the extraction of images of identical time by recording an image along with time at which the image is obtained.

Further, for example, as the necessity of recording of the time of obtaining and extraction of images of identical time may be eliminated by obtaining two images (an anterior eye image and an eye fundus image) at the same timing as an image taken later out of the timing at which the anterior eye image is obtained and the timing at which the eye fundus image is obtained, it is possible to facilitate calculation of the correlation between the moving distance of the anterior eye image and the moving distance of the eye fundus image.

Moreover, instead of controlling of the imaging position, the calculated correlation may be used in correcting positional displacement of an image after the imaging (e.g., the eye fundus image). In this case, it is not necessary to control the imaging position as described above, and the scanning control may be facilitated.

Further, in order to achieve the above object, an ophthalmic device according to another embodiment of the present invention is provided, in which the eye fundus image obtaining means is any one of a fundus camera, an SLO, and an OCT.

It is preferable that any one of a fundus camera, an SLO, and an OCT be selected as the eye fundus image obtaining means depending on a subject or a purpose of the measurement.

Further, by obtaining and recording the correlation between the anterior eye and the eye fundus based on information on an average eye (e.g., normal subject DB), it is possible to control the imaging position (tracking) without using an eye fundus image taken by an SLO, a fundus camera, or the like. Therefore, it is not necessary to provide the eye fundus image obtaining means such as an SLO or a fundus camera if unnecessary, and thus it is possible to achieve simplification of the device (as well as reduction of space and cost).

Moreover, for example, as detection accuracy and a frame rate are different between the SLO image and the anterior eye image, it is possible to control the imaging position at high speed and high accuracy by detecting a component of slow eye movement such as tremor and drift out of components of involuntary eye movement from an high accuracy and low frame-rate SLO image, and a component of quick eye movement such as flick (microsaccade) from a low accuracy and high frame-rate anterior eye image.

Advantageous Effects of Invention

As described above, according to the present invention, as an anterior eye image and an SLO image are used when the OCT imaging is performed, it is possible to perform tracking without depending only on an SLO image. Further, by performing imaging of the anterior eye at timing faster than the SLO imaging and the OCT imaging, it is possible to perform SLO tracking and OCT tracking using an anterior eye image obtained by the imaging of the anterior eye. For example, when performing the OCT imaging at timing faster than the SLO imaging, the OCT tracking may be performed without being restricted to the timing of the SLO imaging, and it is possible to obtain an OCT image that is more accurate and eliminating motion artifact. Moreover, as the OCT imaging may be performed without being restricted to the timing of the SLO imaging, the OCT imaging may be performed at predetermined time intervals. This is effective particularly for Doppler OCT in which the OCT imaging is performed at predetermined time intervals that are very short. Thus, it is possible to provide an ophthalmic device advantageous for three-dimensional OCT images and Doppler OCT.

BRIEF DESCRIPTION OF DRAWINGS

FIG. 7A is a diagram illustrating the example of a B-scan image of an eye fundus, based on OCT, displayed in a monitor of the ophthalmic device according to this embodiment.

FIG. 7B is a diagram illustrating the example of an en-face image (generated from three-dimensional OCT data) of an eye fundus, based on OCT, displayed in a monitor of the ophthalmic device according to this embodiment.

DESCRIPTION OF EMBODIMENT

Embodiment

Hereinafter, an ophthalmic device according to one embodiment of the present invention will be described with reference to the drawings.

One Embodiment

Figure 1:
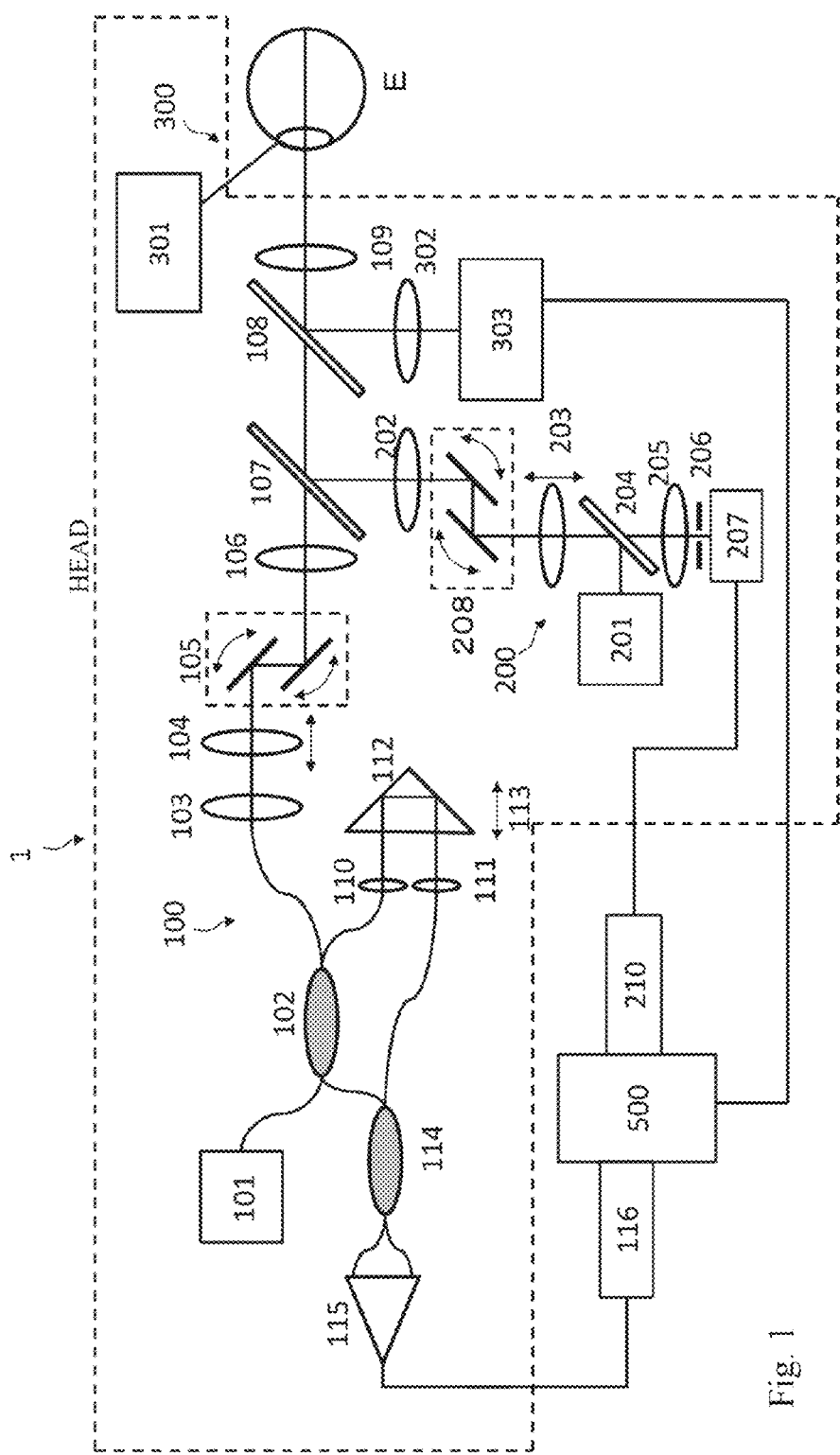
FIG. 1 is a diagram illustrating a configuration of an optical system in one embodiment of an ophthalmic device according to the present invention.
Figure 2:
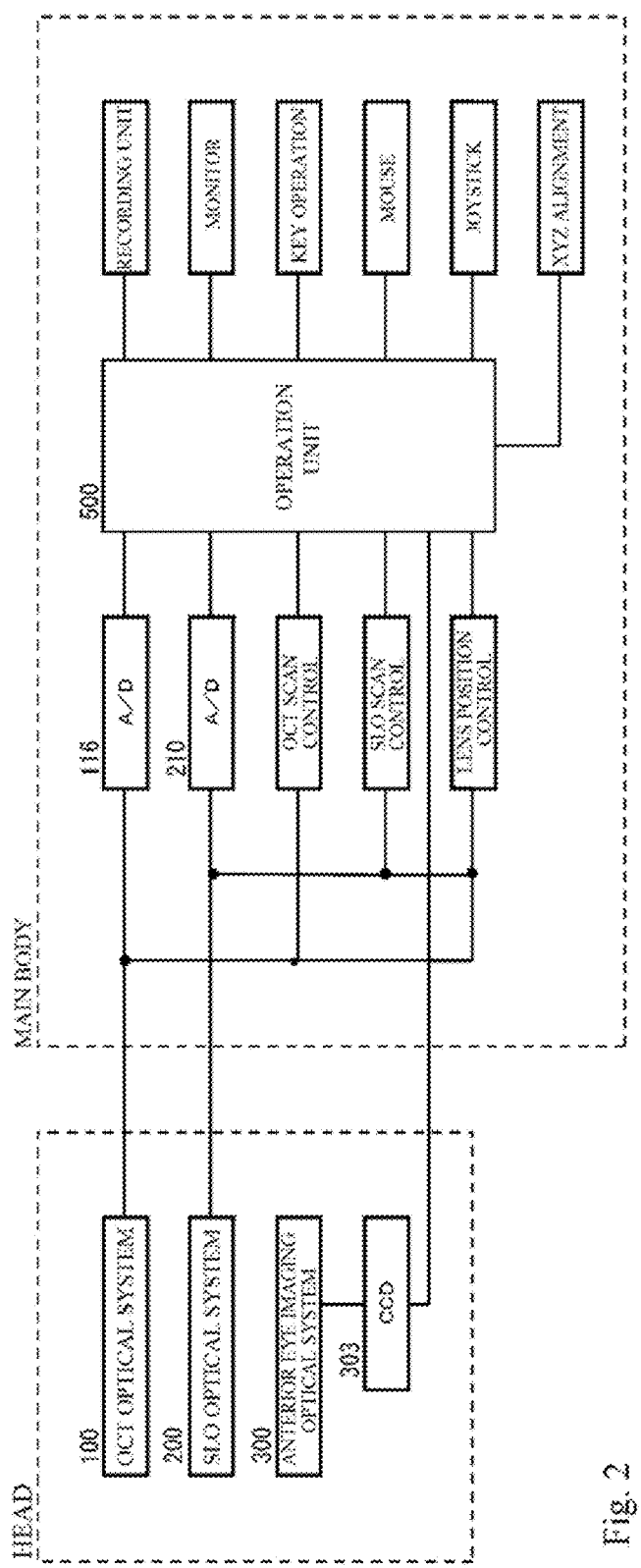
FIG. 2 is a diagram illustrating an entire configuration in one embodiment of the ophthalmic device according to the present invention.

FIG. 1 shows a diagram illustrating an optical system of an ophthalmic device 1 according to the present invention in detail. Then, FIG. 2 shows a diagram illustrating an entire configuration of the device in one embodiment of the ophthalmic device 1 according to the present invention.

The ophthalmic device 1 is provided with three optical systems including: an interference optical system (hereinafter OCT optical system) 100 for non-invasively obtaining a tomographic image of an eye fundus of a subject eye E using a technology with coherent light; a scanning laser ophthalmoscope (SLO) optical system (hereinafter SLO optical system) 200 for irradiating the eye fundus of the subject eye E using an infrared radiation source 201 to obtain an eye fundus SLO image for observation; and an anterior eye imaging optical system 300 for obtaining an anterior eye image by irradiating the anterior eye of the subject eye E using a light source 301.

Configurations of the optical systems will be described in the following. (OCT optical system 100)

The OCT optical system 100 is configured by components from a light source 101 to an ADC 116 for A/D conversion of interference light. In this embodiment, an SS-OCT using a wavelength-swept light source is employed as the light source 101 as one example of Fourier-domain OCT. The SS-OCT is considered to be superior to other OCT methods in terms of its measurement principle in that interference signals (tomographic image data) can be obtained at high speed. The OCT optical system 100 is not limited to the SS-OCT in this embodiment, and may be a different type of Fourier-domain OCT such as a spectral-domain OCT (SD-OCT) or a time-domain OCT.

Light output from the light source 101 split into measurement light input to a collimator lens 103 and reference light input to a collimator lens 110 by a fiber coupler 102 through a fiber. The measurement light input to the collimator lens 103 passes a focus lens 104, a galvoscanner mirror 105, a lens 106, a dichroic mirror 107, a dichroic mirror 108, and an objective lens 109, and is irradiated on an eye fundus of the subject eye E. Then, the measurement light reflected on the eye fundus of the subject eye E is directed, in a manner opposite of the irradiation, through the objective lens 109, the dichroic mirror 108, the dichroic mirror 107, the lens 106, the galvoscanner mirror 105, the focus lens 104, the collimator lens 103, and the fiber coupler 102, and input to one input section of a fiber coupler 114.

The reference light split by the fiber coupler 102 and input to the collimator lens 110 is reflected on a prism 112 and directed through a collimator lens 111 to be input to the other input section of the fiber coupler 114.

The measurement light and the reference light input to the fiber coupler 114 are coupled in the fiber coupler 114, and output as interference light to a balanced detector 115 to be converted into an electric signal (interference signal). Further, the two types of the interference light output from the fiber coupler 114 have phases different from each other by 180 degrees, and the two types of the interference light are input to the balanced detector 115 and amplified in a differential manner. Here, if an influence of a noise content such as a common noise is low, it is possible to use a simple single-input detector, for example.

The interference signal output from the balanced detector 115 is sampled by the ADC 116 as a digital signal, input to an operation unit 500 constituted by a CPU and a memory, transformed by Fourier transformation to obtain an A-scan data as a tomographic signal in a depth direction, and recorded in a memory in the operation unit 500.

The prism 112 is moved along a light axis by a controller 113, so as to control a reference light path length in an alterable and adjustable manner. Normally, prior to the OCT imaging, the prism 112 is moved by the controller 113 so that a reference light path length and a measurement light path length are the same length, and fixed during measurement.

The galvoscanner mirror 105 scans the subject eye E horizontally (in an X axial direction) and vertically (in a Y axial direction), and a control signal is input from the operation unit 500. By scanning using the galvoscanner mirror 105 in the X axial direction and the Y axial direction, it is possible to obtain a three-dimensional tomographic image of the eye fundus of the subject eye E.

In this embodiment, the dichroic mirror 107 is set so as to transmit long-wavelength light having a wavelength of 900 nm or longer (light from the OCT light source 101), for example, and reflect short-wavelength light having a wavelength shorter than 900 nm (e.g., 840 nm, light from the SLO light source). Further, the dichroic mirror 108 is set so as to transmit long-wavelength light having a wavelength of 800 nm or longer (light from the OCT light source 101 or the SLO light source), for example, and reflect short-wavelength light having a wavelength shorter than 800 nm (light from the light source 301 for anterior eye imaging). The dichroic mirrors 107 and 108 are not limited to the above specifications, and may be set adequately according to the wavelength of the light sources to be used.

As described above, using the dichroic mirror 107 and the dichroic mirror 108, the light irradiated on the subject eye E and reflect is split into lights of three different wavelengths (OCT light, SLO light, and anterior eye imaging light) to allow measurement using the lights of the respective wavelengths.

Figure 4:
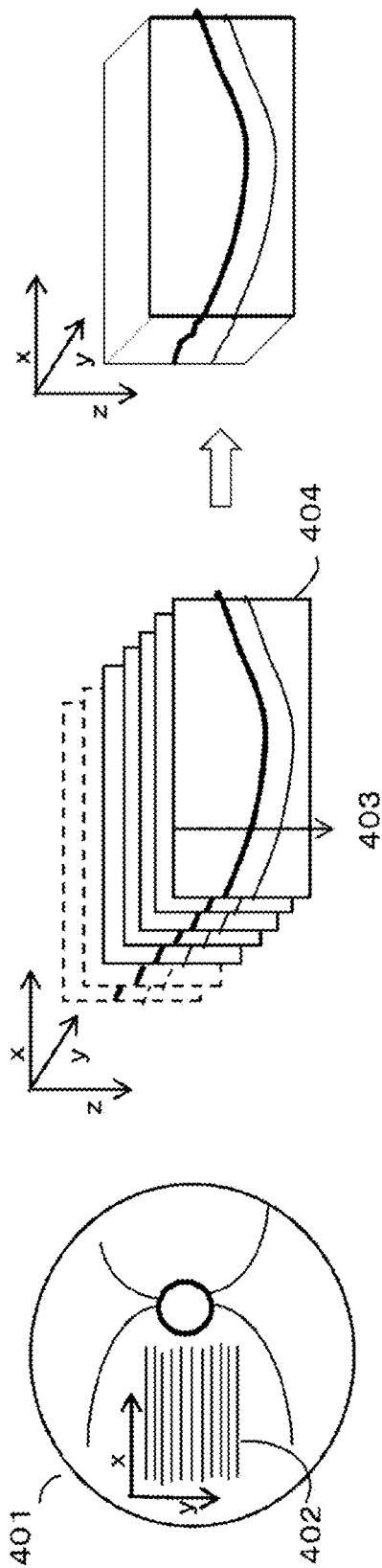
FIG. 4A, FIG. 4B and FIG. 4C are charts showing a flow for obtaining an OCT three-dimensional tomographic view.

FIG. 4A, FIG. 4B and FIG. 4C show how a tomographic view (B-scan image) is obtained by the OCT optical system 100. FIG. 4A shows one example of an eye fundus retina of the subject eye E, and FIG. 4B shows one example of a plurality of two-dimensional tomographic views (B-scan images) of an eye fundus retina 401 obtained using the tomographic view obtaining unit 100. Further, FIG. 4C shows one example of a three-dimensional tomographic view of an eye fundus generated in this embodiment. Here, in FIG. 4A, FIG. 4B and FIG. 4C an x axis indicates a scanning direction for B scan, and a y axis indicates a scanning direction for C scan. Moreover, a z axis in FIGS. 4B and 4C indicates a depth direction of an A scan signal, i.e., a depth direction of the eye fundus. An OCT image that is actually taken and displayed in a monitor is shown in FIG. 7.

(SLO Optical System 200)

The SLO optical system 200 is configured by components from a light source 201 to an ADC 210 as an A/D convertor. Normally, an SLO light source uses an infrared laser diode of 800-900 nm to obtain an eye fundus image non-invasively. Here, a laser diode of 840 nm is used as the SLO light source in this embodiment. The SLO light source is not limited to the laser diode in this embodiment, and may be a different type of light source such as an LED.

Measurement light output from the light source 201 for SLO (hereinafter referred to as SLO measurement light in order to distinguish from other measurement lights) is reflected on a mirror 204. Here, light irradiated on the eye fundus and reflection light reflected on the eye fundus follows the same path. Therefore, a half mirror or a beam splitter, which reflects and transmits light at a predetermined proportion, is employed as the mirror 204 in order to split the light into irradiation light and reflection light. A polarization beam splitter may be employed as the mirror 204, as noise light produced due to unintended scattering and reflection within the optical system is reduced.

Thus, a part of the SLO measurement light is reflected on the mirror 204 and input to the dichroic mirror 107 through a focus lens 203, a scanning device 208, and a lens 202. The input SLO measurement light is reflected on the dichroic mirror 107, transmitted through the dichroic mirror 108 and then the objective lens 109, and irradiated on the eye fundus of the subject eye. The focus lens 203 is controlled to move along the light axis so that the SLO measurement light irradiated on the eye fundus focuses on the eye fundus.

The SLO measurement light reflected on the eye fundus is directed, in a manner opposite of the irradiation, through the objective lens 109, the dichroic mirror 108, the dichroic mirror 107, the lens 202, the scanning device 208, and the focus lens 203, and input to the mirror 204, a part of which light is transmitted through the mirror 204, input to a lens 205, and then to a pinhole 206 after light collection. The light is then received on a light detector 207 and converted into an electric signal to be input to the ADC 210.

Here, similarly to the galvoscanner mirror 105 in the OCT optical system 100, the scanning device 208 scans the SLO measurement light over the eye fundus of the subject eye in the X axial direction and the Y axial direction, and is able to obtain a front image data of the eye fundus by scanning irradiation position of the SLO measurement light by the scanning device 208. The scanning device 208 is not limited to a galvoscanner mirror, and may be a polygon mirror, or may take a configuration in which a galvoscanner mirror and a polygon mirror are combined. Further, as the light detector 207, an avalanche photodiode or a photomultiplier tube may be employed, for example.

Figure 8:
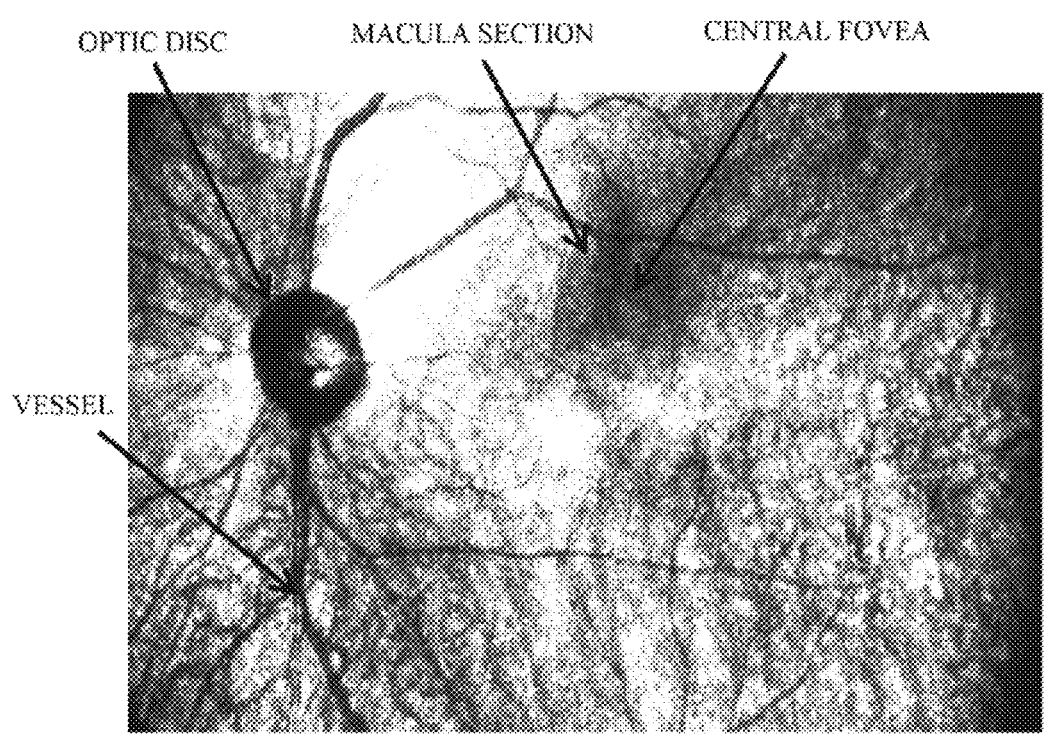
FIG. 8 is illustration of an example of a front image of the eye fundus, based on SLO, displayed in the monitor of the ophthalmic device according to this embodiment.
Figure 9:
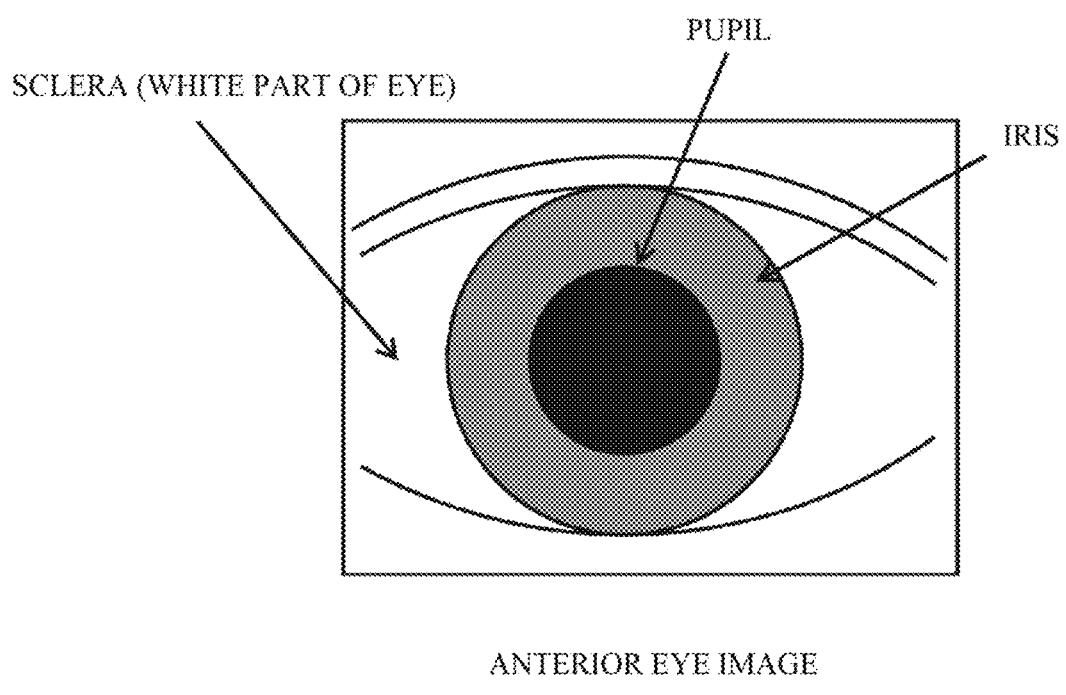
FIG. 9 is illustration of an example of an anterior eye image displayed in the monitor of the ophthalmic device according to this embodiment.

As described above, it is possible to obtain a front image of the eye fundus of the subject eye E by performing X-Y scanning to the eye fundus, sampling the reflection light using the ADC 210, and performing signal processing using the operation unit 500. An SLO image that is actually taken and displayed in the monitor is shown in FIG. 8.

(Anterior Eye Imaging Optical System 300)

The anterior eye imaging optical system 300 is configured by components from the light source 301 to a CCD camera 303 for imaging. A wavelength of the light source 301 for imaging of the anterior eye is not particularly limited, but light having a wavelength shorter than the light for OCT and SLO is selected in this embodiment, as the three optical systems share a part of the light. While visible light may be employed, light of 750 nm is employed in this embodiment in order to reduce the burden on a subject being tested (patient). Further, while an LED is used as the light source, the light source is not limited to this. Moreover, in order to irradiate the anterior eye as a whole evenly with light, the light source 301 may include a lens in addition to the LED.

The light output from the light source 301 irradiates the anterior eye of the subject eye (cornea and entire sclera), takes an anterior eye image of the subject eye by an imaging CCD 303 using the objective lens 109 and a lens 302, and the taken anterior eye image is input to the operation unit 500, and displayed in the monitor shown in FIG. 2, and image processing is performed in the operation unit 500 and movement of the anterior eye is detected, as described later.

(Operational Procedure)

Next, an operational procedure of the ophthalmic device according to this embodiment will be described.

Figure 3:
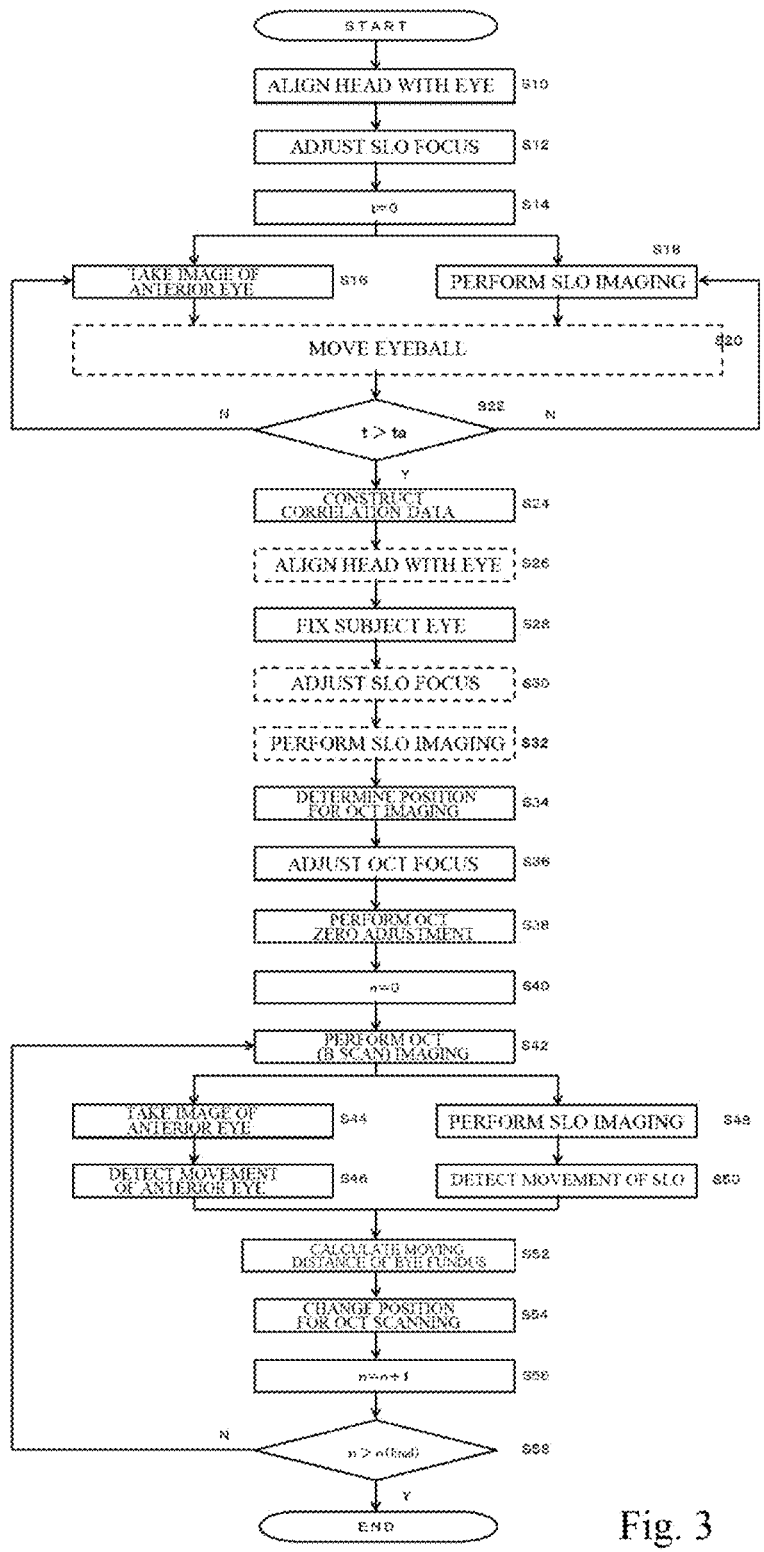
FIG. 3 is a chart showing an operating procedure (flowchart) in one embodiment of the ophthalmic device according to the present invention.

FIG. 3 shows a flowchart explaining the operational procedure in this embodiment. First, in S10, a head (also referred to as a head section) in which the three optical systems are disposed is aligned with an eye of the subject eye (hereinafter referred to as alignment). The alignment is performed using a joystick (not shown) or the like provided for a main body. In this embodiment, in order to facilitate the alignment, the alignment (aligning of the head with the eye) is performed by irradiating a fixation lamp on the subject eye using a fixation optical system (not shown) to a fixation lamp to fix the subject eye. As the fixation optical system, a fixation optical system that is provided for a normal ophthalmic device may be employed.

Next, in S12, a focus of the SLO optical system is adjusted. The focus lens 203 is controlled to move along the light axis so that the SLO light irradiated from the light source 201 focuses on the eye fundus of the subject eye (retina) (focus). Then, a refractive power of the subject eye is calculated based on a value of a control signal obtained at this time, and recorded in a recording unit within the main body.

Next, in the steps from S14 to S22, imaging of the anterior eye (S16) and the SLO imaging (S18) are performed at the same time. The imaging is performed for a predetermined set time period (e.g., 1 second to 2 seconds), and a plurality of anterior eye images and SLO images are obtained during this time period, each of which is recorded with obtained time in the recording unit. Then, during the imaging (S20), using a method such as fixation induction, for example, an eyeball of the subject eye is controlled to move within a predetermined range. Examples of the method of moving the eyeball in S20 include, in addition to fixation induction, a method in which a fixation lamp is turned off and left free without fixation. As one method of fixation induction, fixation induction may be performed by previously providing a plurality of fixation lamps (e.g., 5 to 6 lamps at the center and/or in the circumference) and one of the lamps is turned on in a predetermined order or by selecting randomly.

After the plurality of anterior eye images and the SLO images (the front images of the eye fundus) are obtained in the steps from S14 to S22, correlation between the anterior eye images and the eye fundus images (SLO images) is calculated to construct correlation data in S24. The correlation between the anterior eye images and the eye fundus images (SLO images) is calculated in the following manner. First, characteristic parts of the anterior eye and the eye fundus are set respectively. As the characteristic parts in this case, the center of a pupil, and an outline of a pupil or a cornea, a characteristic vessel in a sclera, a characteristic pattern of an iris, or the like may be set in the case of the anterior eye. In the case of the eye fundus, an optic disc, a central fovea, a position of a characteristic part of the retina vessel, or the like may be set. Then, the set characteristic parts are detected by common image processing such as smoothing and filtering, their positions (coordinates) are calculated for each image, a relation between the previously recorded time and the position coordinate is obtained, a relation between a moving distance in the anterior eye images and a moving distance in the eye fundus image (SLO) is calculated based on a value of the obtained relation, and the calculated relation is recorded as correlation data.

After the correlation data is constructed in S24, the correlation data is recorded in the recording unit, and imaging of a tomographic image of the eye fundus using the OCT optical system 100 starts.

In S26, similarly to S10, the head is again aligned with the eye (aligned). As the head has already been aligned with the eye in S10, the step in S26 is not mandatory, and it is not necessary to align the head with the eye again in S26 if there is no problem in the alignment state (if it is not out of alignment).

Next, the subject eye is fixed using the fixation optical system (not shown) in S28. As described above, the fixation may be performed by the method employed in a common ophthalmic device, or by providing a more effective fixation optical system.

Then, imaging of a front image of the eye fundus by SLO is performed in order to determine a position at which the tomographic image of the eye fundus is obtained by the OCT optical system 100.

In S30, similarly to S12, a focus of the SLO optical system is adjusted. The detailed operation is omitted here, as it is described above. Here, the step in S30 is not mandatory, either, and it is not necessary to adjust the focus again if there is no problem in the focused state of the SLO optical system (the focus position is right).

Then, in S32, the SLO imaging is performed to obtain the front image of the eye fundus. As the SLO imaging is performed in S18, the SLO imaging may be performed consecutively. In other words, as the SLO imaging has been already performed in the step in S18, the steps from S30 to S32 are not mandatory, and may be included in the operational procedure as needed.

After the front image of the eye fundus is obtained in S32, the front image of the eye fundus is displayed in the monitor (not shown). The display may be real-time display, or the images may be displayed by switching by an operation of an examiner. Then, in S34, the examiner looking at the front image of the eye fundus displayed in the monitor determines an imaging position (position of the eye fundus) in the OCT imaging. The determination may be made by the examiner while looking at the monitor. If the imaging position is previously determined (such as the position at or around the optic disc or the central fovea), the imaging position for the OCT imaging may be determined by having the operation unit 500 analyze the front image of the eye fundus by SLO and automatically detecting the imaging position.

After the imaging position in the OCT imaging is determined, a focus in OCT is adjusted in S36. The focus is adjusted by controlling the position of the focus lens 104 by moving the focus lens 104 along the light axis such that the light from OCT focuses on the eye fundus (retina) as a position of a subject of imaging.

After the focus adjustment in OCT is completed, zero adjustment in OCT is performed in S38. The zero adjustment is performed by controlling the prism 112 in the reference optical system to move along the light axis such that in the OCT optical system, measurement light path length, as a light path length of a measure optical system (for irradiating light on the subject eye to obtain the reflection light), and reference light path length, as a light path length of a reference optical system described above, become identical. While the prism 112 is employed in this embodiment, it is not limited to the prism, and a mirror or the like may be employed.

After the zero adjustment in OCT is completed in S38, setting of "n=0" is made in S40. In this embodiment, in order to obtain a three-dimensional tomographic (graphical)

image, the number is counted taking a first obtained B-scan graphical image as a 0-th image to perform C scan (move the position) and to obtain a plurality of B-scan graphical images.

Then, the OCT imaging starts in S42. In the case of SS-OCT which is Fourier-domain OCT as in this embodiment, scanning in the depth direction (Z direction) is not necessary, and because a plurality of A-scan images (also referred to as one-dimensional tomographic views) within the scanned range may be obtained by having the galvoscanner mirror 105 scan once in the X direction or Y direction, the OCT imaging is hereinafter used synonymously with B-scan imaging in this embodiment. Further, an image by the OCT imaging is referred to as a B-scan image or a B-scan graphical image. In this embodiment, the B-scan graphical image is a two-dimensional tomographic (graphical) image of the eye fundus in the depth direction. Then, operations from S42 to S58 described below are repeated until a previously set number (i.e., a predetermined number n (final)) of images are obtained.

The OCT imaging (synonymous with B-scan imaging) is performed at the same time as the imaging of the anterior eye (S44) and the SLO imaging (S48). Then, the OCT imaging is performed while performing detection of movement of the anterior eye (S46) and detection of movement of the eye fundus (S50) based on the anterior eye images and the SLO images obtained in the imaging of the anterior eye (S44) and the SLO imaging (S48), and calculating and recording information on the movement of the anterior eye (moving distance) and information on the movement of the eye fundus (moving distance). A detail of the method relating to the detection of movement of the anterior eye (S46) and the detection of movement of the eye fundus (S50) is not described here, as it will be described later.

Then, in S52, a moving distance of the eye fundus is calculated by using the information on the movement obtained by the detection of movement of the anterior eye (S46) and the detection of movement of the eye fundus (S50) and by using the correlation data constructed in S24. A detail of the method of calculation is not described here, as it will be described later.

In S56, based on the moving distance of the eye fundus calculated in S52, the position in OCT for scanning control is altered and a next OCT image is taken (n=n+1).

If the number of the taken images is a predetermined number (S58, n>n (final)), the OCT imaging is completed. If the number of the taken images is less than the predetermined number, the process returns to S42, and the OCT imaging is continued.

As described above, by the operational flow in FIG. 3 according to the present invention, it is possible to obtain accurate three-dimensional tomographic images of the eye fundus of the subject eye E.

(Construction of Correlation Data of Moving Distances of Anterior Eye Image and Eye Fundus Image)

Figure 5:
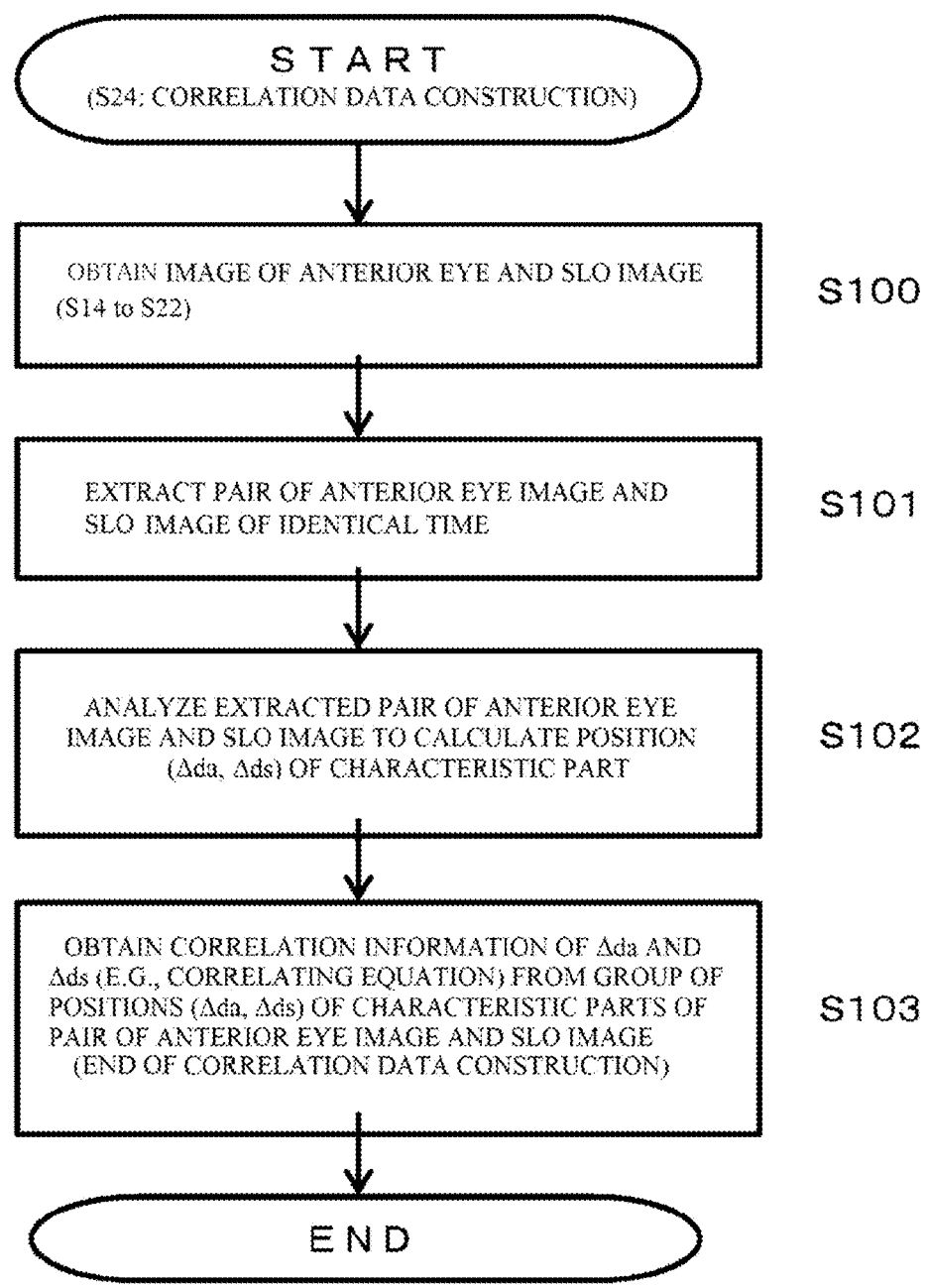
FIG. 5 is a flowchart showing procedures for construction of correlation data of moving distances between an anterior eye image and an eye fundus image (S24 in FIG. 3).
Figures 6A, 6B, 6C:
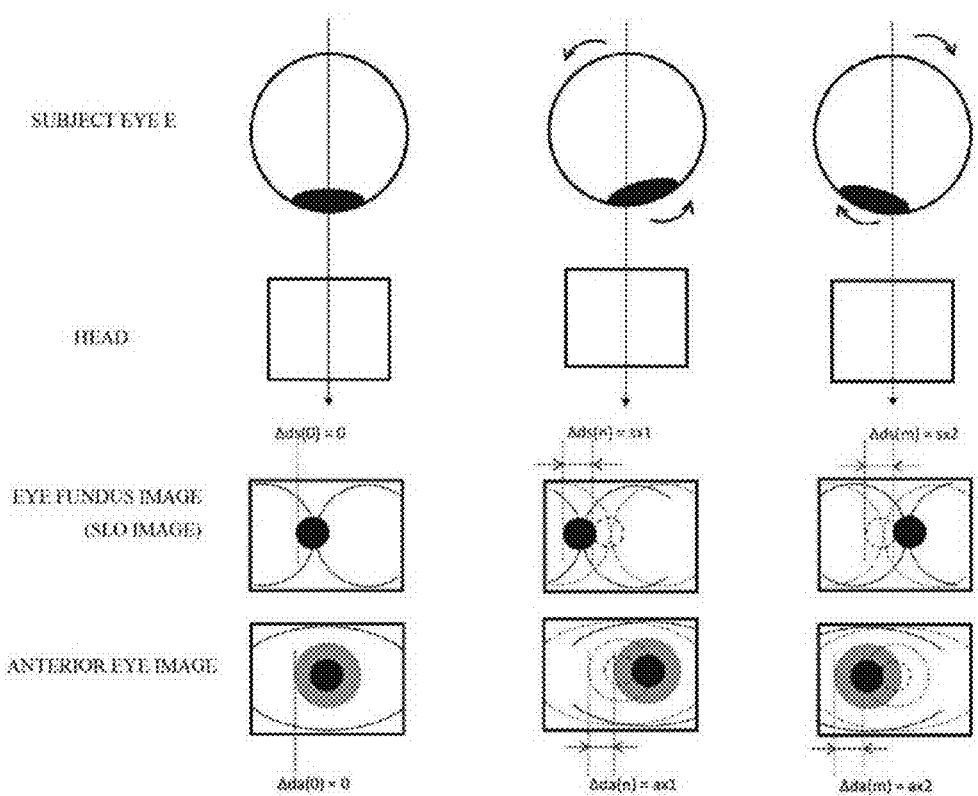
FIG. 6A, FIG. 6B and FIG. 6C are diagrams illustrating relation between movement of an eyeball, an anterior eye image, and an eye fundus image (SLO image).

FIG. 5 shows flowchart showing procedures for construction of the correlation data of moving distances of the anterior eye image and the eye fundus image (S24 in FIG. 3). Further, FIG. 6A, FIG. 6B and FIG. 6C show relation between movement of the eyeball, the anterior eye image, and the eye fundus image (SLO image). Moreover, FIGS. 10A, 10B, 10C and FIGS. 11A, 11B, 11C show how the anterior eye and the eye fundus move, and timing of the imaging of the anterior eye and the SLO imaging performed in the steps from S14 to S22 shown in FIG. 3. The procedures for construction of correlation data (S24 in FIG. 3) are described with reference to FIGS. 5, 6A, 6B, 6C, 10A, 10B, 11A, 11B, and 12.

Figures 10A, 10B:
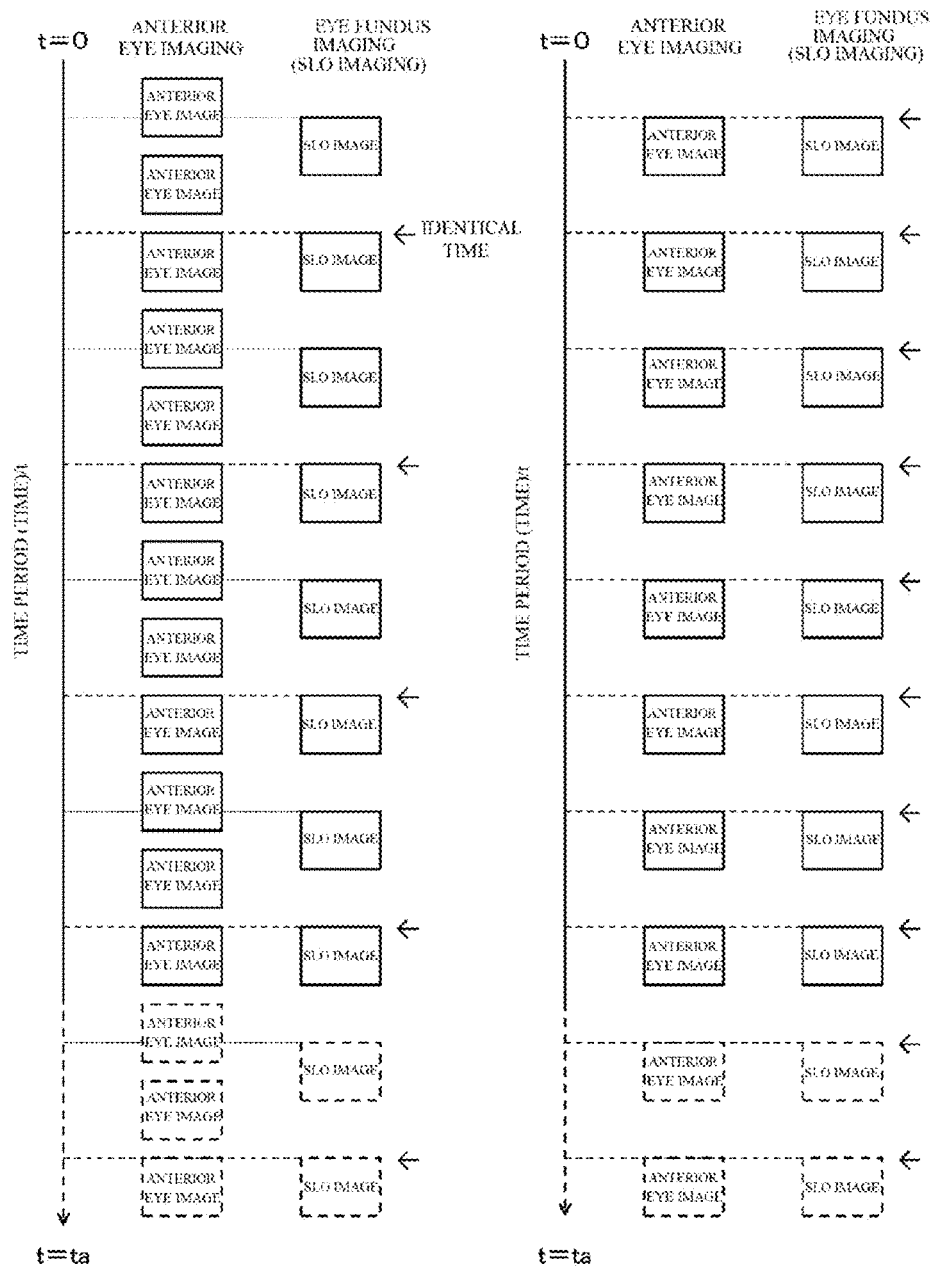
FIG. 10A and FIG. 10B are diagrams illustrating how anterior eye imaging and SLO imaging are performed in S14 to S22 in the flowchart in FIG. 3.
Figure 11A:
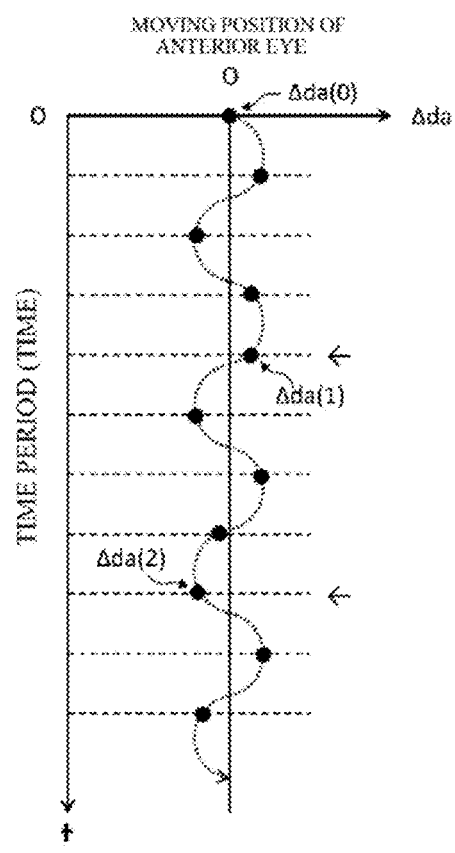
FIG. 11A is a chart showing how the anterior eye moves and timing of imaging when anterior eye imaging and SLO imaging are performed in S14 to S22 in the flowchart in FIG. 3.
Figure 11B:
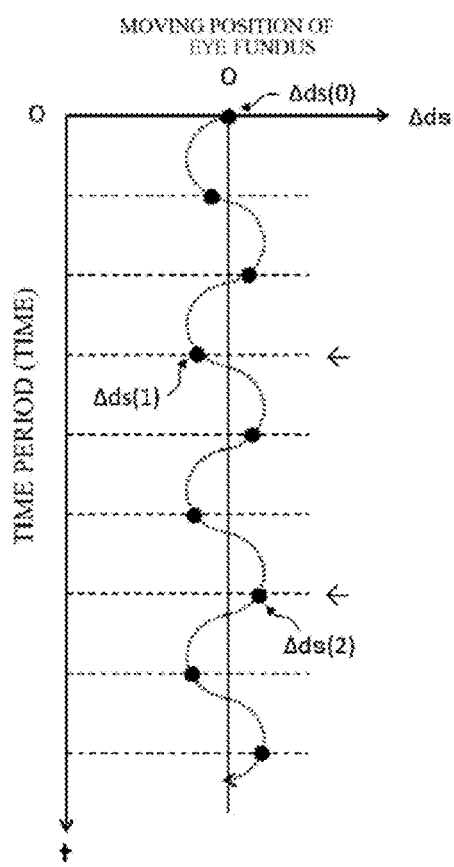
FIG. 11B is a chart showing how the eye fundus moves and timing of imaging when anterior eye imaging and SLO imaging are performed in S14 to S22 in the flowchart in FIG. 3.

In S100 (S14 to S22), the plurality of anterior eye images and SLO images (eye fundus images) are taken during a predetermined time period. FIG. 10A and FIG. 10B show how the images are obtained. The method for obtaining images may be performed in a variety of manners. In a method shown in FIG. 10A, for example, the imaging of the anterior eye (S16) and the SLO imaging (S18) are performed separately. Then, data at time (t), at which an image is obtained (time data), is also obtained at the same time in the obtaining, and recorded in the recording unit along with the obtained image data.

After a plurality of anterior eye images with time data and SLO images are obtained in S100, in S101, a pair of an anterior eye image and an SLO image having the same time data is extracted from a group of the anterior eye images and the SLO image that have been obtained.

Next, in S102, image analysis of the extracted pair of the anterior eye image and the SLO image is performed, and positions ($\Delta da$, $\Delta ds$) of previously set characteristic parts of the anterior eye and the eye fundus are calculated. Here, $\Delta da$ is a moving position of the anterior eye, and $\Delta ds$ is a moving position of the eye fundus.

FIG. 6A, FIG. 6B and FIG. 6C show a method of calculating $\Delta da$ and $\Delta ds$. FIG. 6A, FIG. 6B and FIG. 6C shows an example in which a position of an outline of the cornea is set as the characteristic part of the anterior eye, and a position of an outline of the optic disc is set as the characteristic part of the eye fundus. The characteristic part that is set is not limited to the example of FIG. 6A, FIG. 6B and FIG. 6C as described above, and may be set depending on a condition of the eye of the subject being tested.

FIG. 6A is a diagram illustrating the subject eye E, the anterior eye image, and the eye fundus image immediately after the alignment in S10. $\Delta da$ and $\Delta ds$ at this time are taken as 0 (zero) ($\Delta da(0)=0$, $\Delta ds(0)=0$).

FIG. 6B is a diagram illustrating the subject eye E, the anterior eye image, and the eye fundus image when the subject eye E turns leftward. As the subject eye is in a spherical shape, the eye fundus moves rightward if the anterior eye moves leftward. Accordingly, the characteristic part of the anterior eye image moves leftward by $\Delta da(n)$, and the characteristic part of the eye fundus image moves rightward by $\Delta ds(n)$.

FIG. 6C is a diagram illustrating the subject eye E, the anterior eye image, and the eye fundus image when the subject eye E turns rightward. As described above, the subject eye is in a spherical shape, and therefore the eye fundus moves leftward when the anterior eye moves rightward. Accordingly, the characteristic part of the anterior eye image moves leftward by $\Delta da(m)$, and the characteristic part of the eye fundus image moves rightward by $\Delta ds(m)$.

As described above, in S103, correlation information of $\Delta da$ and $\Delta ds$ is obtained from $\Delta da$ and $\Delta ds$ pair $D(n)=(\Delta da(n), \Delta ds(n))$ of the plurality pairs of the anterior eye image and the SLO image extracted in S102. (Completing construction of the correlation data).

Figure 12:
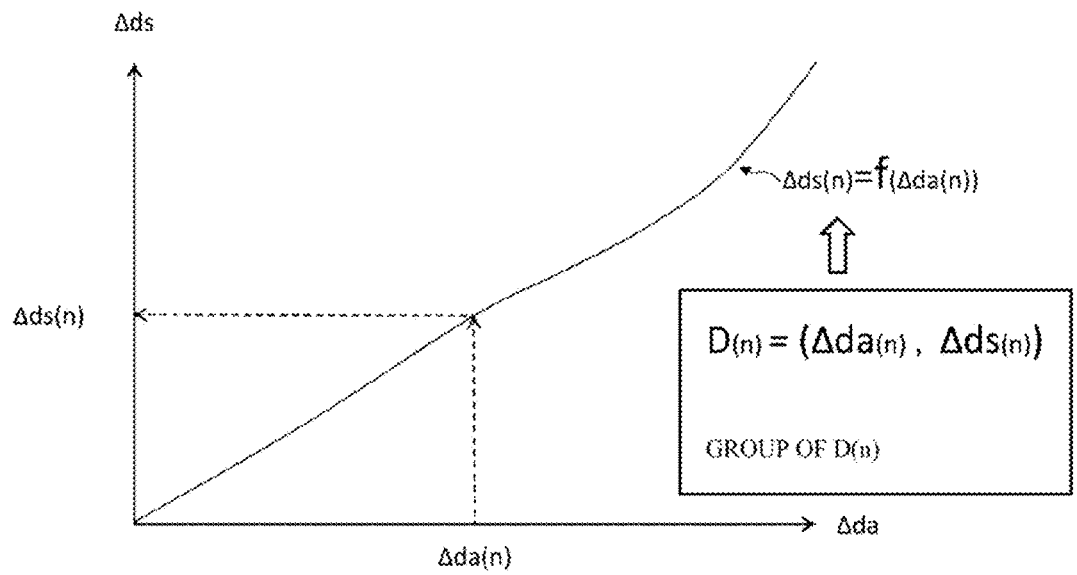
FIG. 12 is a correlation chart between a moving position of the anterior eye and a moving position of the eye fundus in one embodiment of the ophthalmic device according to the present invention.

As the correlation information of $\Delta da$ and $\Delta ds$, as shown in FIG. 12, a correlating equation $\Delta ds(n)=f(\Delta da(n))$ of the moving position of the anterior eye and the moving position of the eye fundus may be obtained. By obtaining and recording such a correlating equation in the recording unit, it is possible to facilitate the calculation when the moving distance of the eye fundus is calculated in S52 in FIG. 3.

FIG. 12 shows, but not limited to, one embodiment of the correlation data (between the moving distance of the anterior eye image and the moving distance of the eye fundus image) according to the present invention.

Further, while the method of FIG. 10A is employed in the above example when a plurality of the anterior eye images and the SLO images (eye fundus images) are obtained during a predetermined time period in S100 (S14 to S22), but it is possible to obtain the anterior eye images at imaging timing for the SLO images for which the sampling speed is low as in a method of FIG. 10B. In this case, the time data for the time (t) is not necessary, and it is not necessary to detect the pairs as in S101. Therefore, it is possible to easily construct the correlation data as compared to the example in FIG. 10A.

Further, in the above description, when the moving distance of the eye fundus is calculated in S52 in FIG. 3, the moving distance of the eye fundus is calculated based on the correlating equation $\Delta ds(n)=f(\Delta da(n))$ obtained in S103. However, a new correlating equation $\Delta ds(n)=f(\Delta da(n))$ may be obtained by performing the SLO imaging at the same time as the imaging of the anterior eye as in the steps from S44 to S50 in FIG. 3, and the moving distance of the eye fundus may be calculated based on these two correlating equations.

Moreover, the present invention is not limited to the above description, and if the anterior eye image and the SLO image are obtained at the same timing when the SLO imaging is performed at the same time as the imaging of the anterior eye as in the steps from S44 to S50 in FIG. 3, it is possible to use $\Delta da$ and $\Delta ds$ at this time.

In the above embodiment, the example in which two-dimensional and three-dimensional tomographic images are obtained using an intensity signal of the interference light is described. However, as described below, the method of controlling the OCT scanning according to the present invention is also advantageous in Doppler OCT in which blood flow speed is measured.

The method disclosed in Japanese Publication No. 2008-29467, in which an SLO eye fundus image is obtained every time when a single OCT B-scan graphical image is obtained, performs the OCT imaging synchronously with intervals for obtaining the SLO eye fundus images. Therefore, the OCT imaging affects the intervals for obtaining the SLO eye fundus images, and may often not be employed in the Doppler OCT in which the OCT imaging is performed at a predetermined time period.

By contrast, in the method according to the present invention, the OCT imaging (mainly represents obtaining of B-scan graphical images) may be performed regardless of the SLO imaging as in the above embodiment. In other words, as the time periods for the OCT imaging may be freely set, the OCT imaging in the Doppler OCT in which the OCT imaging is performed at a predetermined time period in order to measure the blood flow speed. Further, by controlling the OCT scanning according to the present invention, it is possible to measure a blood flow speed more accurately based on Doppler.

As described above, by using the method according to the present invention, it is possible to obtain B-scan graphical images at high speed while eliminating the positional displacement due to the movement of the subject eye.

While the detailed description has been given to the embodiment of the present invention described above, it is understood that the description is a mere example, and the present invention is not construed as being limited by any specific description in the embodiment, and may be implemented in any manner with or without various alterations, modifications, and improvements based on a person skilled in the art. It is also understood that any such implementations without departing from the present invention are also included in the scope of the present invention.

For example, while SLO is used to take the eye fundus image in the above embodiment, the imaging of the eye fundus is not limited to SLO, and it is possible to use a fundus camera or the like.

Further, while the imaging of the anterior eye and the SLO imaging are performed for a predetermined time period in the steps from S14 to S22, a plurality of fixation lamps that are not in the drawings may be used for the fixation induction. For example, it is possible to perform fixation induction by providing a fixation optical system having a plurality of fixation lamps at the center and/or in the circumference and turning on one of the lamps in a predetermined order or randomly, and the subject eye moves in a certain range. By performing fixation induction in this manner, $\Delta da$ and $\Delta ds$ may be obtained at different moving distances, and it is possible to obtain more accurate correlation information.

Further, unlike the above example, without using fixation induction, it is possible to employ a method of allowing the subject eye to freely move by turning off a fixation lamp so as not to allow fixation.

Moreover, while the correlation data between the moving distance of the anterior eye and the moving distance of the eye fundus is constructed before the OCT imaging in the above embodiment, the construction of the correlation data is not limited to the above method, and the correlation data may be constructed using correlation between the anterior eye and the eye fundus based on information on average data of eye (e.g., normal subject DB), and recorded in the recording unit. In this case, an optical system for the eye fundus imaging is not a mandatory component, and may be added if necessary.

Furthermore, scanning in the OCT imaging is controlled using the constructed correlation data in the above embodiment, but an obtained OCT image may be corrected using the correlation data. In this case, it is possible to facilitate the scanning control.

Although the invention has been described in detail with particular reference to these preferred embodiments, other embodiments can achieve the same results. Variations and modifications of the present invention will be obvious to those skilled in the art and it is intended to cover in the appended claims all such modification and equivalents. The entire disclosures of all references, applications, patents, and publications cited above are hereby incorporated by reference.

REFERENCE SIGNS LIST

1: Ophthalmic device of this embodiment
100: OCT optical system
101: Light source
102: Fiber coupler
105: Galvoscanner mirror
107, 108: Dichroic mirror
112: Prism
200: SLO optical system
201: SLO light source
204: Beam splitter
208: SLO scanning device
300: Anterior eye imaging optical system 303: CCD camera
500: Operation unit
E: Subject eye

The invention claimed is:

1. An ophthalmic device comprising:
anterior eye image obtaining means configured to obtain an image of an anterior eye of a subject eye;
eye fundus image obtaining means configured to obtain an image of an eye fundus of the subject eye;
correlation calculating means configured to calculate correlation between a moving distance of the subject eye in the anterior eye image and a moving distance in the eye fundus image; and
control means configured to control a position for imaging of the eye fundus image by the at least one eye fundus image obtaining means based on the moving distance of the eye fundus image calculated from the moving distance of the subject eye in the anterior eye image using the correlation calculated by the correlation calculating means and/or the moving distance of the eye fundus image calculated from the eye fundus image obtained by the eye fundus image obtaining means.

2. The ophthalmic device according to claim 1, wherein the eye fundus image obtaining means includes at least two eye fundus image obtaining means each configured to obtain an image of the eye fundus of the subject eye, and the correlation calculating means calculates correlation between the moving distance of the subject eye obtained by the anterior eye image obtaining means and a moving distance in the eye fundus image taken by one of the at least two eye fundus image obtaining means.

3. The ophthalmic device according to claim 2, additionally comprising positional displacement correction means configured to perform correction of positional displacement of the eye fundus image after imaging by the at least one eye fundus image obtaining means based on the moving distance of the eye fundus image calculated from the moving distance of the subject eye in the anterior eye image using the correlation calculated by the correlation calculating means and/or the moving distance of the eye fundus image calculated from the eye fundus image obtained by the eye fundus image obtaining means.

4. The ophthalmic device according to claim 2, wherein the correlation calculating means includes calculating means configured to obtain a plurality of anterior eye images (by the anterior eye image obtaining means) and a plurality of eye fundus images (by the at least one eye fundus image obtaining means) for a predetermined time period, and to calculate correlation between a moving distance of the subject eye and a moving distance in the eye fundus image (due to the movement of the subject eye) from the plurality of obtained anterior eye images and the plurality of obtained eye fundus images.

5. The ophthalmic device according to claim 4, wherein when obtaining and recording the plurality of anterior eye images and the plurality of eye fundus images (by the at least one eye fundus image obtaining means), the correlation calculating means also records time of the obtaining.

6. The ophthalmic device according to claim 1, additionally comprising positional displacement correction means configured to perform correction of positional displacement of the eye fundus image after imaging by the at least one eye fundus image obtaining means based on the moving distance of the eye fundus image calculated from the moving distance of the subject eye in the anterior eye image using the correlation calculated by the correlation calculating means and/or the moving distance of the eye fundus image calculated from the eye fundus image obtained by the eye fundus image obtaining means.

7. The ophthalmic device according to claim 1, wherein the correlation calculating means includes calculating means configured to obtain a plurality of anterior eye images (by the anterior eye image obtaining means) and a plurality of eye fundus images (by the at least one eye fundus image obtaining means) for a predetermined time period, and to calculate correlation between a moving distance of the subject eye and a moving distance in the eye fundus image (due to the movement of the subject eye) from the plurality of obtained anterior eye images and the plurality of obtained eye fundus images.

8. The ophthalmic device according to claim 7, wherein when obtaining and recording the plurality of anterior eye images and the plurality of eye fundus images (by the at least one eye fundus image obtaining means), the correlation calculating means also records time of the obtaining.

9. The ophthalmic device according to claim 8, wherein the correlation calculating means obtains the anterior eye images and the eye fundus images (by the at least one eye fundus image obtaining means) at the same time at at least two different times.

10. The ophthalmic device according to claim 7, wherein the correlation calculating means obtains the anterior eye images and the eye fundus images (by the at least one eye fundus image obtaining means) at the same time at at least two different times.

11. The ophthalmic device according to claim 1, wherein the eye fundus image obtaining means is any one of a fundus camera, an SLO, and an OCT.

12. The ophthalmic device according to claim 1, wherein the ophthalmic device is an OCT imaging device for ophthalmology including a fundus camera or an SLO as means of obtaining a front image of the eye fundus.

* * * * *